US011903848B2

(12) United States Patent
Beyer

(10) Patent No.: US 11,903,848 B2
(45) Date of Patent: Feb. 20, 2024

(54) SPINAL CAGE HAMMER

(71) Applicant: Neo Medical SA, La Villette (CH)

(72) Inventor: Morten Beyer, Rødkærsbro (DK)

(73) Assignee: NEO MEDICAL SA, La Villette (CH)

( * ) Notice: Subject to any disclaimer, the term of this patent is extended or adjusted under 35 U.S.C. 154(b) by 160 days.

(21) Appl. No.: 17/287,127

(22) PCT Filed: Nov. 8, 2019

(86) PCT No.: PCT/IB2019/059612
§ 371 (c)(1),
(2) Date: Apr. 21, 2021

(87) PCT Pub. No.: WO2020/095261
PCT Pub. Date: May 14, 2020

(65) Prior Publication Data
US 2021/0386560 A1 Dec. 16, 2021

(30) Foreign Application Priority Data

Nov. 8, 2018 (WO) .................. PCT/IB2018/058784

(51) Int. Cl.
*A61F 2/48* (2006.01)
*A61F 2/46* (2006.01)
(52) U.S. Cl.
CPC ..... *A61F 2/4611* (2013.01); *A61F 2002/4681* (2013.01)
(58) Field of Classification Search
CPC ... A61F 2/46; A61F 2/4611; A61F 2002/4681
See application file for complete search history.

(56) References Cited

U.S. PATENT DOCUMENTS 4,971,479 A * 11/1990 Byers, Sr. .............. E01F 9/608
173/90
5,505,732 A 4/1996 Michelson
5,913,860 A * 6/1999 Scholl .................. A61B 17/921
606/86 R
(Continued)

FOREIGN PATENT DOCUMENTS

CN 113194886 A * 7/2021 ............ A61F 2/4611
EP 3799843 A1 * 4/2021 ............ A61F 2/4611
(Continued)

OTHER PUBLICATIONS

International Search Report dated Mar. 19, 2020, for Application No. PCT/IB2019/059612.
(Continued)

*Primary Examiner* — Eric S Gibson
(74) *Attorney, Agent, or Firm* — NIXON & VANDERHYE

(57) ABSTRACT

The present invention concerns a spinal cage hammer including an elongated body comprising a proximal end and a distal end, the elongated body extending from the proximal end to the distal end and defining a cavity extending from the proximal end to the distal end, the at least one cavity being configured to receive at least one portion of a spinal cage holder for holding a spinal cage. The spinal cage hammer includes an interface wall or surface configured to enter into contact with the spinal cage holder to transfer a force to the spinal cage holder.

12 Claims, 9 Drawing Sheets

(56) References Cited

U.S. PATENT DOCUMENTS

| | | | | |
|---|---|---|---|---|
| 6,063,124 | A * | 5/2000 | Amstutz | A61F 2/3603 |
| | | | | 623/22.21 |
| 6,814,738 | B2 * | 11/2004 | Naughton | A61F 2/4603 |
| | | | | 606/100 |
| D786,031 | S * | 5/2017 | Whitten | D8/14 |
| 10,695,194 | B2 * | 6/2020 | Robinson | A61F 2/4611 |
| 11,583,418 | B2 * | 2/2023 | Robinson | A61F 2/4611 |
| 2003/0055434 | A1 * | 3/2003 | O'Neil | A61F 2/4611 |
| | | | | 606/100 |
| 2005/0240197 | A1 * | 10/2005 | Kmiec | A61B 17/921 |
| | | | | 606/100 |
| 2010/0145461 | A1 | 6/2010 | Landry et al. | |
| 2018/0140438 | A1 * | 5/2018 | Robinson | A61F 2/4611 |
| 2020/0315814 | A1 * | 10/2020 | Robinson | A61F 2/4611 |
| 2021/0100660 | A1 * | 4/2021 | Lequette | A61F 2/4684 |
| 2021/0169661 | A1 * | 6/2021 | Beck | A61F 2/4609 |
| 2021/0386560 | A1 * | 12/2021 | Beyer | A61F 2/4611 |
| 2022/0323238 | A1 * | 10/2022 | El-Chafei | A61F 2/367 |

FOREIGN PATENT DOCUMENTS

| | | |
|---|---|---|
| JP | H08-506501 A | 7/1996 |
| JP | 2002-248109 A | 9/2002 |
| WO | 94/17759 A1 | 8/1994 |
| WO | WO-2020095261 A1 * | 5/2020 ............ A61F 2/4611 |

OTHER PUBLICATIONS

Written Opinion of the ISA dated Mar. 19, 2020, for Application No. PCT/IB2019/059612.
Office Action issued in Japanese Patent Application No. 2021-521470 dated Jul. 25, 2023.

* cited by examiner

SPINAL CAGE HAMMER

CROSS REFERENCE TO RELATED APPLICATIONS

The present application is a United States national stage application of International patent application PCT/IB2019/059612 filed on Nov. 8, 2019 designating the United States, and claims foreign priority to International patent application PCT/IB2018/058784 filed on Nov. 8, 2018, the contents of both documents being herewith incorporated by reference in their entirety.

FIELD OF THE INVENTION

The present invention concerns a spinal cage hammer or spinal cage holder hammer and more particularly a spinal cage hammer or spinal cage holder hammer configured to apply a force to a spinal cage holder to position a spinal cage, for example, in a human body for instance in the spine or between two vertebrae.

BACKGROUND

A spinal cage holder is used for handling or manipulating a spine cage used, for example, for spinal fusion between two or more vertebrae of the spine.

A spinal cage held by the holder (sometimes called an interbody cage) is used in spinal surgery, for example, for restore spinal alignment. The cage can, for example, be placed in the disc space between two vertebrae, for example, for the purpose of restoring lost disc height resulting from a collapsed disc and to relieve pressure on nerve roots.

The spinal cage holder is a device configured to hold the cage permitting the cage to be placed in a desired location in, for example, the spine of a patient. The spinal cage holder is, for example, configured to provisionally hold the cage and release the cage once the cage has been located in a desired position in the body of a patient.

During the insertion or placement of a spine cage between vertebrae of a patient it is often necessary to force the cage into a desired position between vertebrae thus requiring a mechanical force or force by physical contact or impact to be applied by hammering on an end of a spinal cage holder to which a spinal cage is attached, the spinal cage being attached, for example at an opposing end to that to which the hammering force is applied.

Spinal cage holders require repeated application of such hammering to be applied to the spinal cage holder to achieve a correct placement or positioning of the spine cage.

However, it is difficult to precisely apply a hammering force or impact of a desired amplitude and direction to the spinal cage holder and as a result the insertion and correct placement of a spine cage often requires a higher quantity of repeated hammering and/or adjustment than should normally be required resulting in a prolonged operation time and a prolonged effort required by the Surgeon to achieve correct placement of the spinal cage.

SUMMARY

The goal of the present invention is to provide a spinal cage hammer or spinal cage holder hammer that overcomes the above-mentioned inconvenience. In particular, the goal of the present invention is to assure that a Surgeon can achieve correct placement of the spinal cage in, for example, the spine of a patient with a reduced hammering effort or adjustment.

The present invention is thus a spinal cage hammer according to claim 1. The spinal cage hammer according to the present invention advantageously allows a hammering force of desired amplitude and direction or a more controlled amplitude and direction to be applied to the spinal cage holder to allowing a spinal cage to be more easily placed in a desired position, for example, inside the spine of a patient.

The spinal cage hammer advantageously makes it much easier for a Surgeon to apply a force in a linear direction to the spinal cage holder and spinal cage thus permitting a more refined or controlled handling of the displacement and positioning of the spinal cage.

The spinal cage hammer also advantageously allows a Surgeon to apply a force of a desired amplitude in the linear direction to the spinal cage holder and spinal cage thus permitting a more refined or controlled handling of the displacement and positioning of the spinal cage.

The present invention also concerns a spinal cage system including the spinal cage hammer and/or a spinal cage.

Other advantageous features can be found in the dependent claims.

A BRIEF DESCRIPTION OF THE SEVERAL VIEWS OF THE DRAWINGS

FIGS. 1 and 2 are schematic representations showing a non-limiting and exemplary embodiment of a spinal cage system of the present disclosure. FIG. 2 shows an enlarged view of an upper part of the spinal cage system illustrated and highlighted by a bracket in FIG. 1.

FIGS. 3 to 8 as well as FIGS. 9A to 9D and FIGS. 10A to 10E show non-limiting and exemplary embodiments of spinal cage hammers of the present disclosure. FIGS. 3 to 5 are side-views, FIGS. 6 and 7 are top-views from the top or proximal end (end closest to the user) of a spinal cage hammer and FIG. 8 is a bottom view from the bottom or distal end (end furthest from the user) of a spinal cage hammer.

FIG. 10A is a bottom view, FIG. 10B is a top view, FIGS. 10C and 10D are side views of opposite sides and FIG. 10E is a cross-sectional view.

Herein, identical reference numerals are used, where possible, to designate identical elements that are common to the Figures.

DETAILED DESCRIPTION OF THE SEVERAL EMBODIMENTS

An exemplary spinal cage hammer 1, spinal cage holder hammer or hammer for a spinal cage holder 1 according to the present disclosure is shown, for example, in FIGS. 1 to 8, as well as in FIGS. 9A to 9D and FIGS. 10A to 10E.

Figure 1:
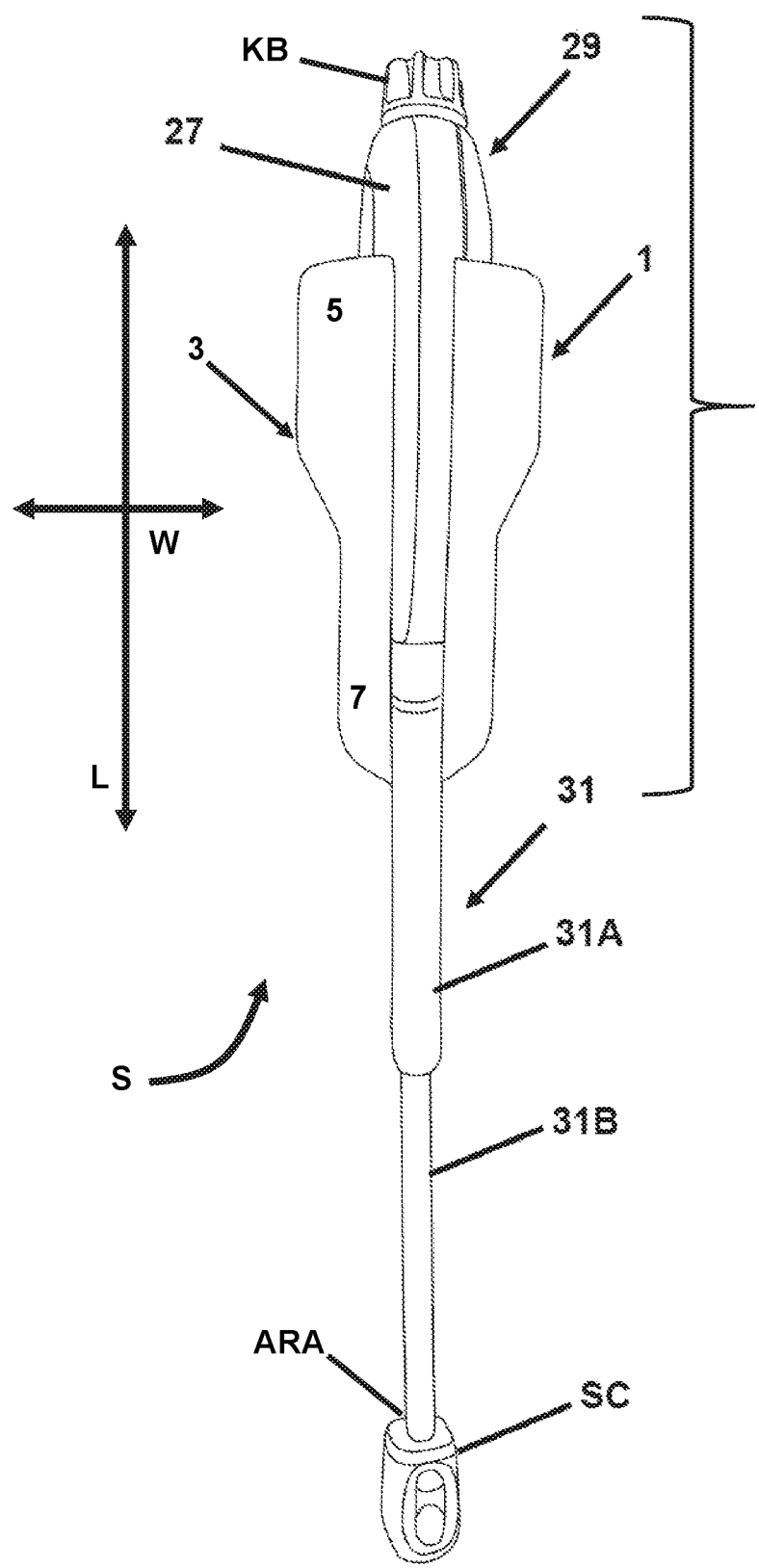
Figure 2:
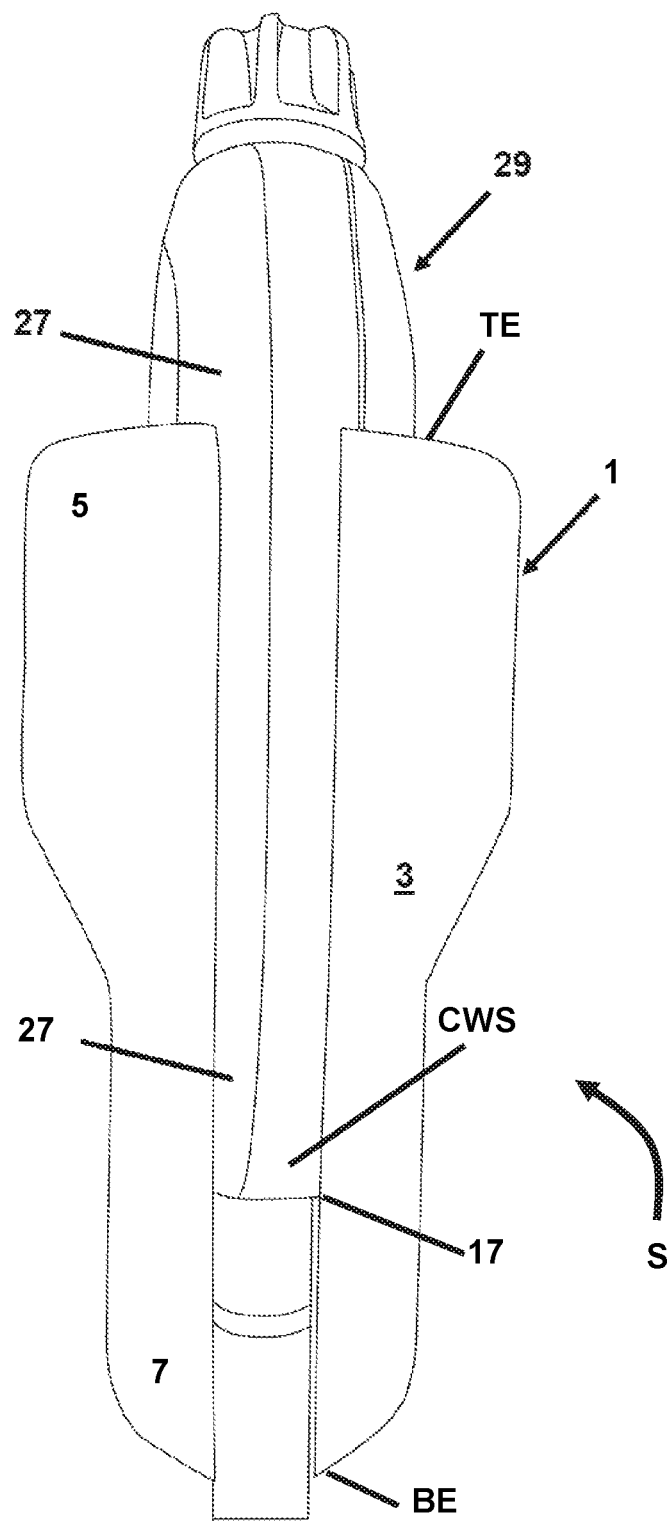
Figure 3:
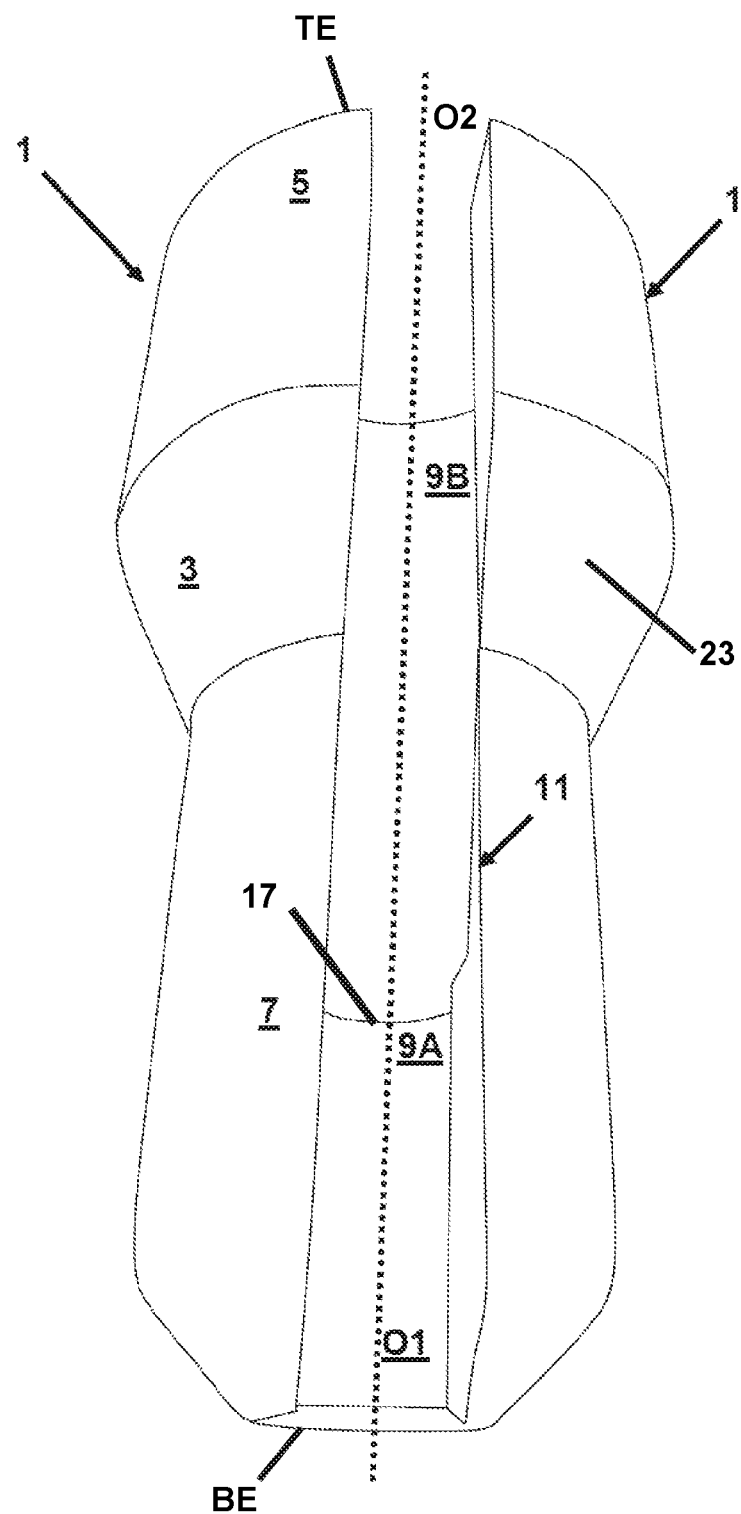
Figure 4:
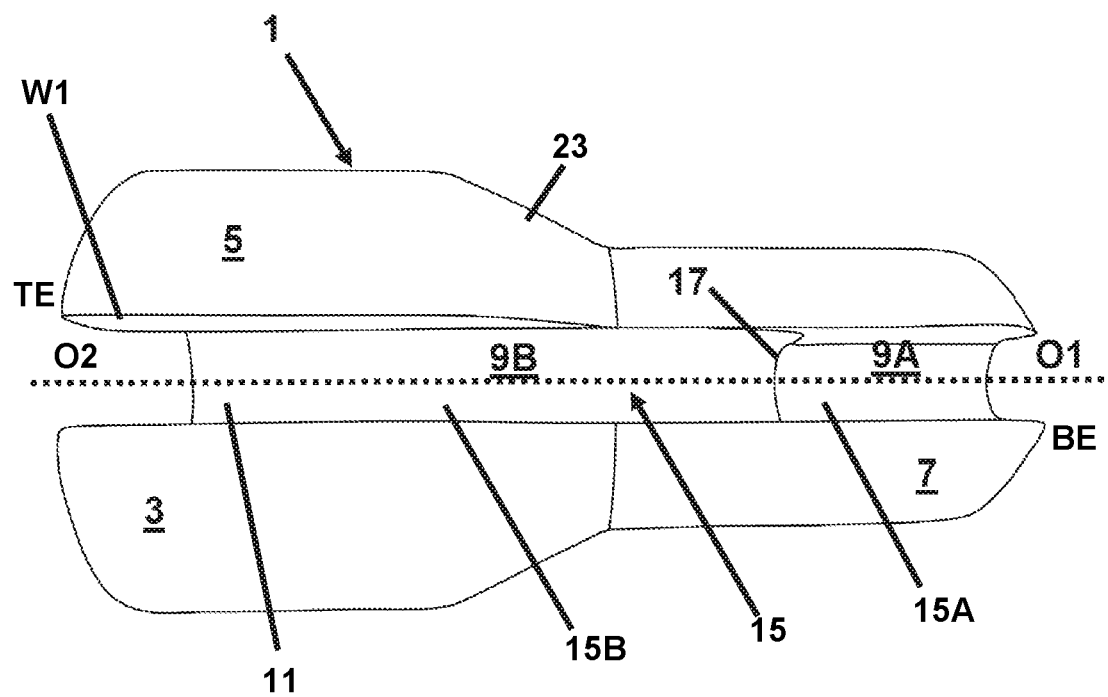
Figure 5:
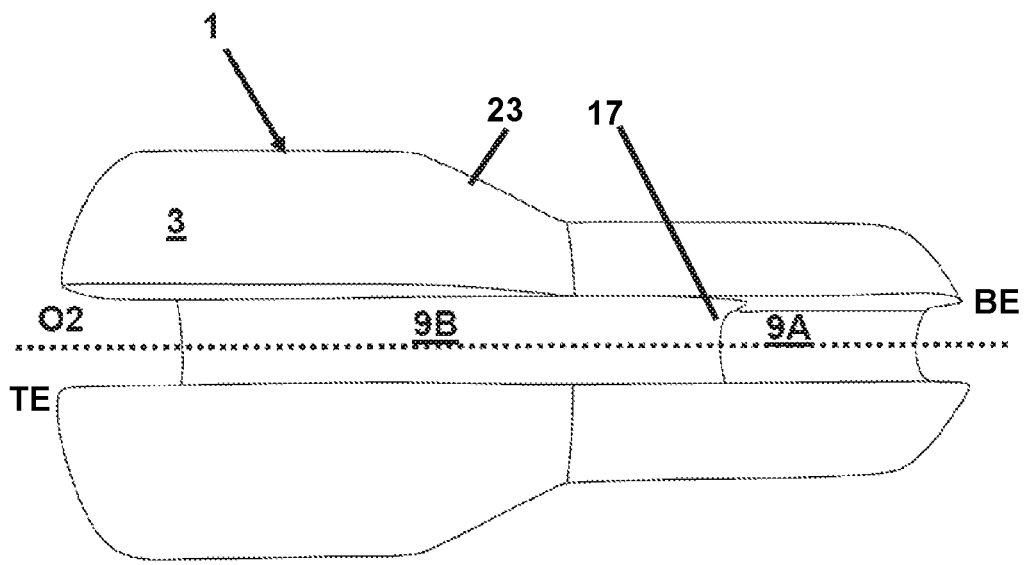

FIGS. 1 and 2 schematically show embodiments of a system, spinal system or spinal cage system S including the spinal cage hammer 1 of the present disclosure as well as a device configured to hold a cage or spinal cage SC, for example, a spinal cage holder 29. The system may also include the spinal cage SC.

The spinal cage hammer 1, or hammer for a spinal cage holder 1 is a device for applying a force to the holder 29 via a mechanical or kinetic force, or a force applied by physical contact or impact of the hammer with the holder 29.

The spinal cage is a spinal implant or device (or intervertebral implant or device) for implantation in the spine, for example, a human spine. As previously mentioned, the cage or spinal cage SC held by the holder 29 (sometimes called an interbody cage) is used in spinal surgery, for example, for restore spinal alignment. The cage SC can, for example, be placed in the disc space between two vertebrae, for example, for the purpose of restoring lost disc height resulting from a collapsed disc and to relieve pressure on nerve roots.

The spinal cage holder 29 is a device configured to hold the cage SC permitting the cage SC to be placed in a desired location in, for example, the spine of a patient. The spinal cage holder 29 is, for example, configured to provisionally hold the cage 29 and release the cage SC once the cage SC has been located in a desired position in the body of a patient.

Figure 11:
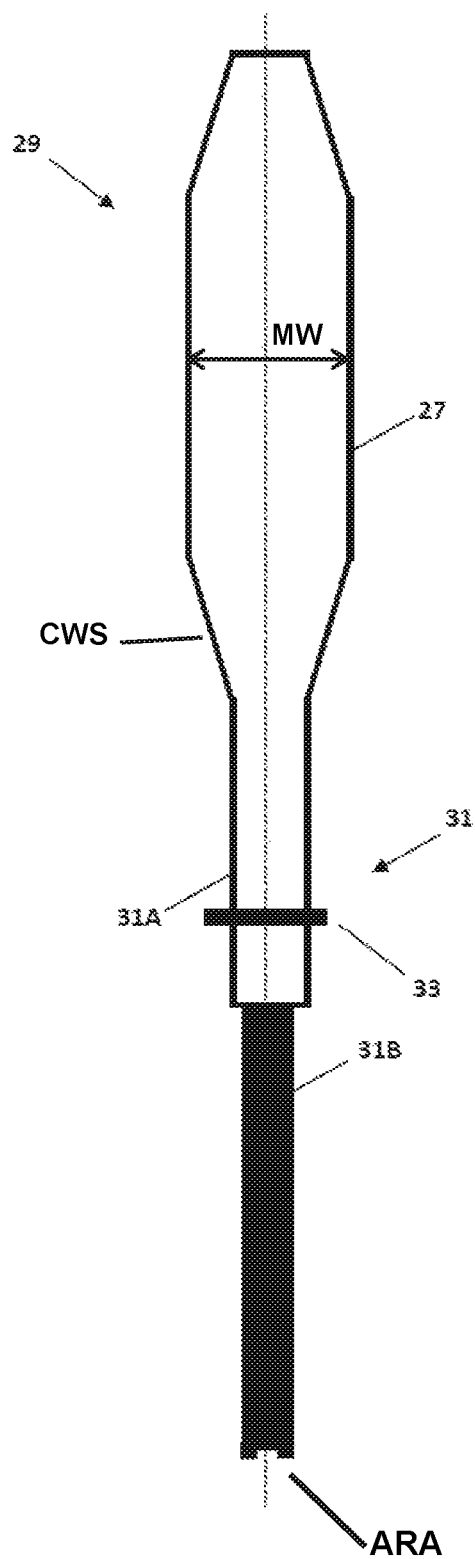
FIG. 11 shows another non-limiting and exemplary embodiment of a spinal cage holder of a system or spinal cage system of the present disclosure.

FIGS. 1 and 11 show non-limiting exemplary examples of the holder 29. The holder 29 is configured to hold the cage SC at an extremity of the holder 29, for example, the distal extremity furthest from the user or closest to a patient. The spinal cage hammer 1 includes an elongated body 3 comprising a proximal end 5 (end closest to the user) and a distal end 7 (end furthest from the user). The elongated body 3 extends from the proximal end 5 to the distal end 7. The elongated body 3 defines a cavity or at least one cavity or chamber 9, 9A, 9B (see, for example, FIG. 3) extending from the proximal end 5 to the distal end 7.

The cavity 9 or cavities 9A, 9B extends fully through the body 3 from the proximal end 5 to the distal end 7 to pass entirely through the body 3 from an outer lower or bottom extremity BE of the body 3 to an outer upper or top extremity TE of the body 3. It is thus possible to see entirely through the body 3 and to the outside when the user is looking through the proximal end 5 or the distal end 7.

Figure 9A:
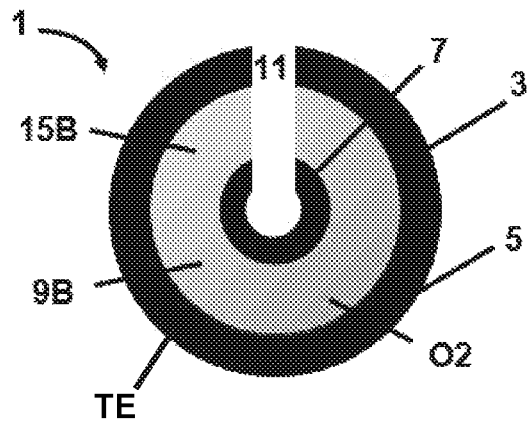
FIG. 9A is a top view.
Figure 9B:
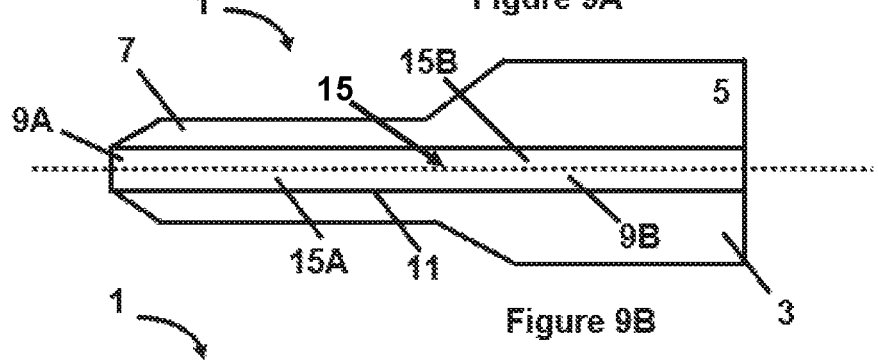
FIGS. 9B and 9C are side views of opposite sides and FIG. 9D is a cross-sectional view of a hammer comprising an internal interface wall or surface for interaction with a spinal cage holder.
Figure 9C:
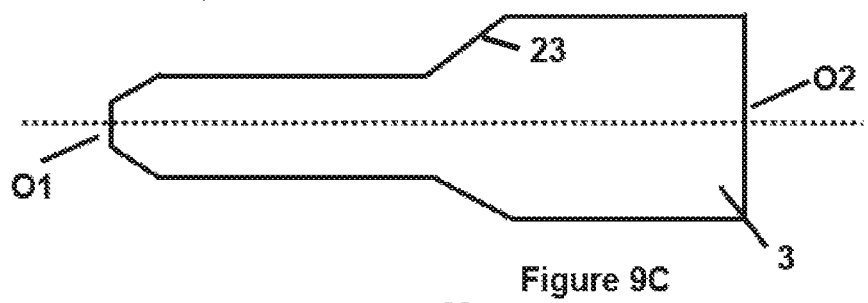
Figure 9D:
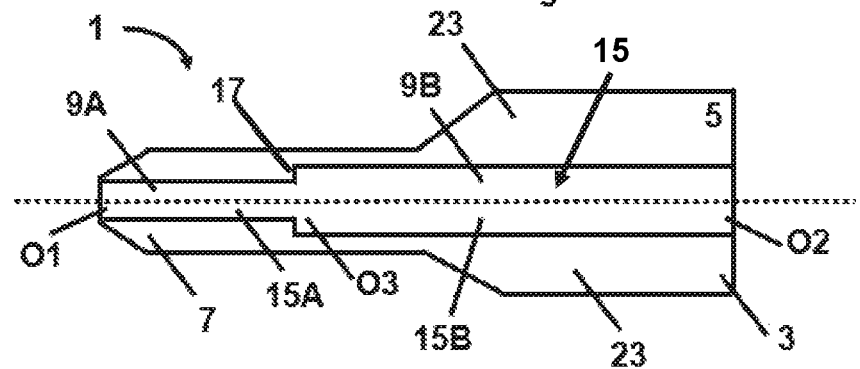

FIG. 9D shows an exemplary embodiment in which the hammer 1 includes a first cavity 9A and a second cavity 9B defining different volumes and that are interconnected and directly communicating with each other. The first cavity 9A and the second cavity 9B have different widths or diameters W, where the width or diameter W extends in a direction (substantially) perpendicular to a longitudinal direction or a direction of elongation L of the hammer 1. FIGS. 1 to 8 also show a hammer 1 comprising this feature.

The hammer 1 may additionally include further cavities having different widths or diameters W to that the first cavity 9A and/or the second cavity 9B.

Figure 10A:
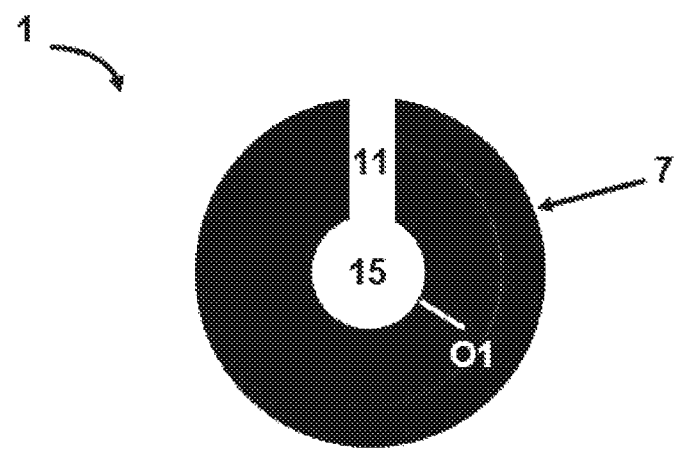
FIGS. 10A to 10E show another non-limiting and exemplary embodiment of a spinal cage hammer of the present disclosure in which a hammer comprises an external interface wall or surface.
Figure 10B:
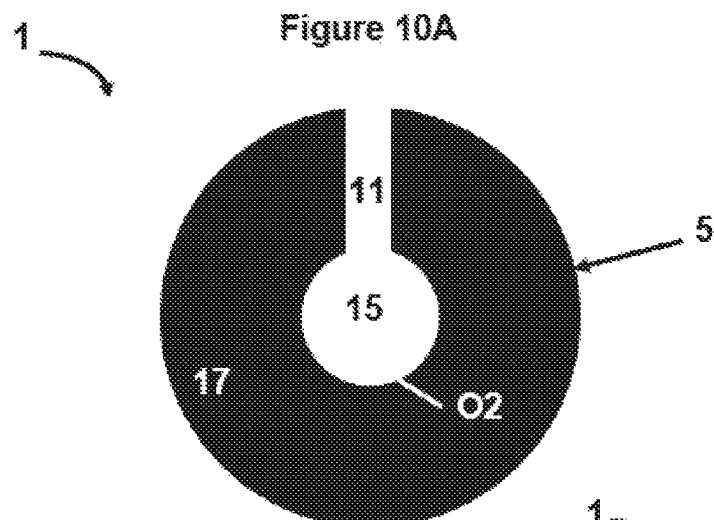
Figure 10C:
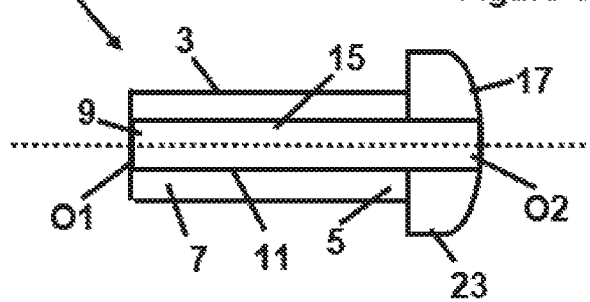
Figure 10D:
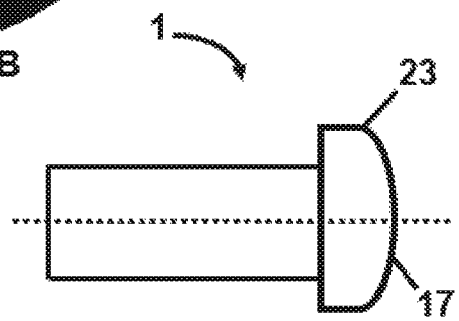
Figure 10E:
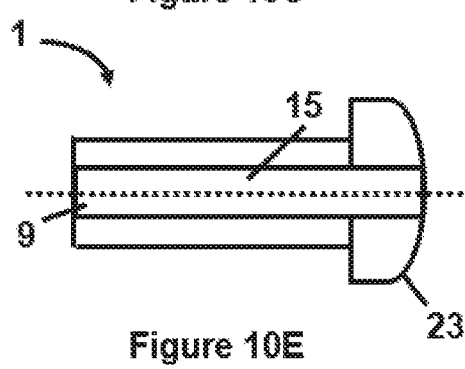

FIG. 10E shows an embodiment of the hammer 1 in which the cavity 9 has (substantially) the same width or diameter W, or, in other words, the first cavity 9A and the second cavity 9B have (substantially) the same width or diameter W. The first cavity 9A and the second cavity 9B of the embodiment of FIG. 9D may, in an alternative embodiment, have (substantially) the same width or diameter W. The spinal cage hammer 1 in a preferred embodiment may also include a slit or elongated aperture 11 extending into the cavity from the proximal end 5 to the distal end 7 (see, for example, FIG. 3).

The spinal cage hammer 1 thus can include the elongated body 3 comprising the proximal end 5 and the distal end 7, the elongated body 3 extending from the proximal end 5 to the distal end 7 and defining the at least one cavity 9, 9A, 9B extending from the proximal end 5 to the distal end 7, and the slit 11 extending into the cavity 9 from the proximal end 5 to the distal end 7.

Figure 6:
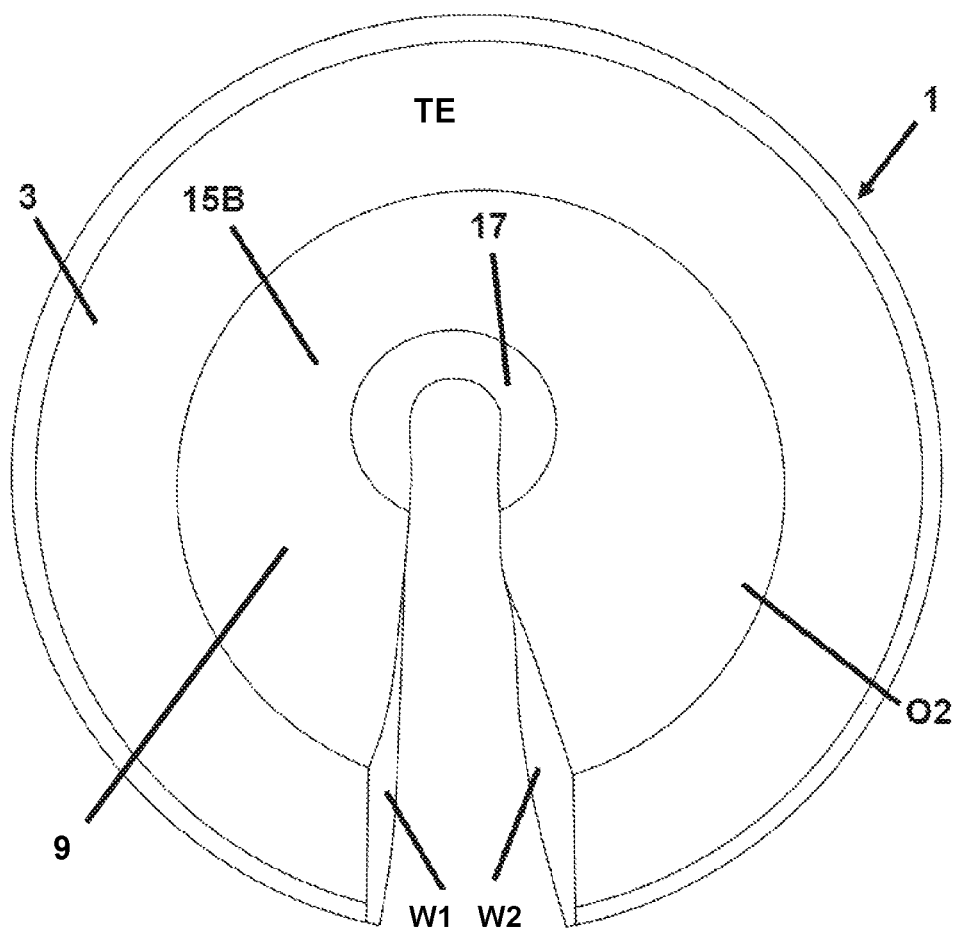
Figure 7:
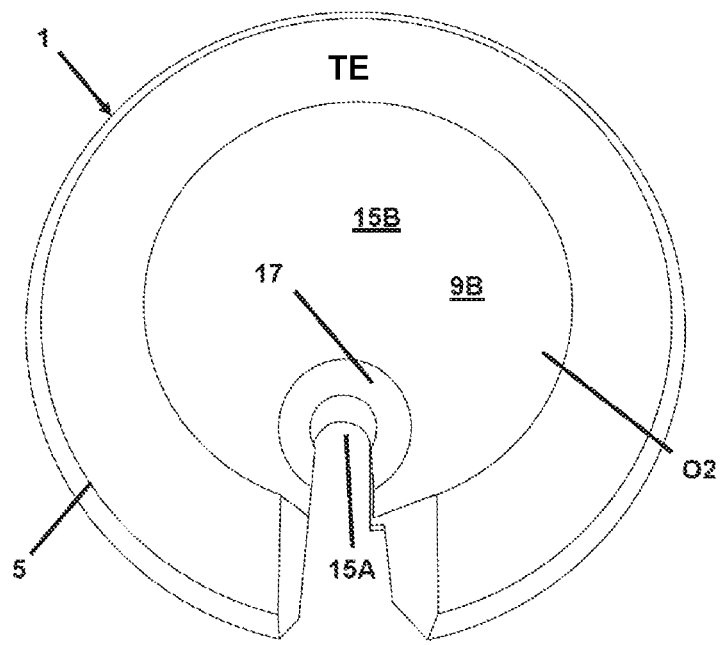
Figure 8:
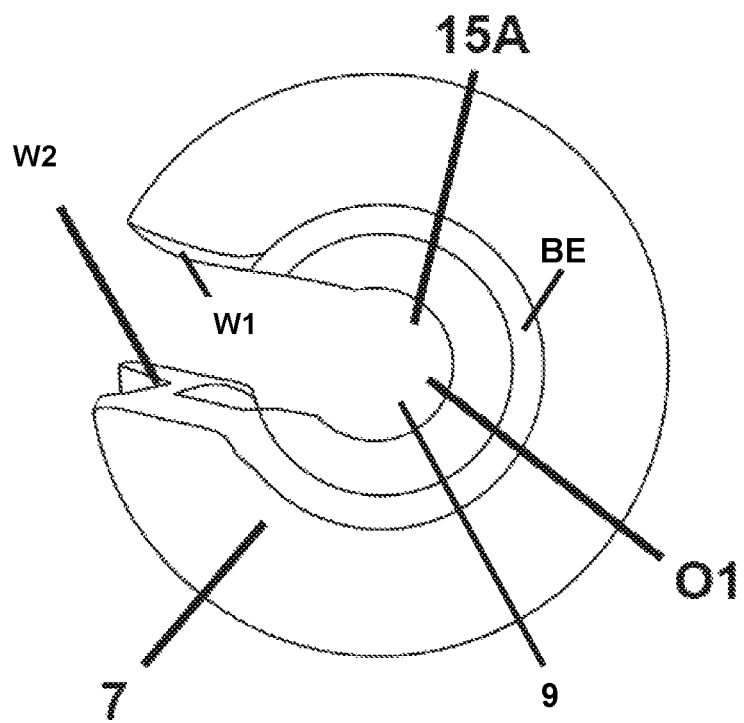

The slit or elongated aperture 11 is defined by at least one wall of the body 3, for example, a first wall W1 and a second wall W2 of the body 3 that extend fully along the elongated length of the body from the upper outer extremity TE to the bottom outer extremity TB (see, for example, FIG. 6).

The at least one wall can, for example, extend inwards into the body 3 to also delimit the at least one cavity or cavities 9, 9A, 9B.

The slit 11 extends fully through the body 3 from an outer surface of the body 3 inwards through the body 3 to the cavity 9 or cavities 9A, 9B. The slit or elongated aperture 11 delimits an opening into the cavity 9 or cavities 9A, 9B. The cavity 9 or cavities 9A, 9B are visible to the user through the slit 11.

The slit 11 also fully extends along the elongation direction L of the body 3 from the outer lower or bottom extremity BE of the body 3 to the outer upper or top extremity TE of the body 3.

The slit 11 can, for example, delimit an opening having a width (extending (substantially) in a direction W (substantially) perpendicular to the direction of elongation L of the body 3) that is larger (or slightly larger, for example, between 5 to 10% larger) than the width or diameter of a shaft 31 of the holder 29 or at least one portion (for example, first or lower portion 31B closest to the spinal cage SC or holding position of the cage SC) of the shaft 31 of the spinal cage holder 29 (see for example FIGS. 1 and 11). This allows for insertion or easy insertion of the spinal cage holder 29 into the spinal cage hammer 1 by passage of the shaft or the portion of the shaft 31 through the slit 11 when the slit 11 and shaft (or shaft portion) are aligned or substantially aligned with each other (or at a small angle, for example, less than 45°) in an elongated manner.

The length (in the direction of elongation of the body 3) of the slit 11 can, for example, be equal to or less than that of the length of the shaft 31 of the holder 29, or than that of the lower shaft portion 31B of the shaft 31 of the holder. This also allows for easy insertion of the spinal cage holder into the spinal cage hammer 1.

A second or upper portion 31A of the shaft 31 of the spinal cage holder 29 (see, for example, FIGS. 1 and 11) may have a diameter or width larger than that of the lower portion 31B of the shaft 31, for example, 5% to 15% larger. In such a case, the opening delimited by the slit 11 may have a width that is larger (or slightly larger, for example, between 5 to 10% larger) than the width or diameter of the lower portion 31B of the shaft 31 of the holder 29. This facilitates insertion via the lower portion 31B. The upper portion 31A can be received in the cavity 9 of the hammer 1 and the cavity 9 is configured to guide the movement of the hammer 1 relative to the holder 29, for example, to define a linear movement of the hammer 1 relative to the holder 29. The hammer 1 can be guided slidably along the holder 29.

The cavity 9, 9A (or a portion of the cavity) may have a width or diameter W slightly larger than (for example, between 1% and 10% or 20%, or between 3% and 10% or 20%, or between 5% and 10% or 20%) the width or diameter of the shaft 31 or the upper portion 31A of the shaft 31 to permit the shaft 31 to slide and be guided in the cavity. This permits the hammer 1 to be guided linearly and/or guided slidably along the holder 29.

In another embodiment, the spinal cage hammer 1 may not comprise the slit or elongated aperture 11 and can be slit-less or elongated aperture-less. In such an embodiment, the hammer 1 may for example resemble, on all sides, the hammer 1 shown in FIG. 9C or 10D. The body 3 defines an outer surface or wall that is circumferentially continuous or whose outer boundary is continuous, at least along a portion of the body 3. In such a case, the shaft 31 is inserted via the upper outer extremity TE and may require the cage SC to be absent and attached after post-insertion. The cavity 9 is nevertheless configured to guide the displacement of the hammer 1 relative to the holder 29 and the shaft 31, permitting the hammer 1 to be guided linearly and/or guided slidably along the holder 29, as mentioned previously.

The spinal cage hammer 1 may, for example, define or have a cylindrical shape or have an outer funnel shape. The spinal cage hammer 1 may for example be made of, comprise or consist of a plastic or a polymer. The spinal cage hammer 1 is for example made of, comprises or consists of a polyvinyl chloride (PVC), polyethylene, a polyester, polycarbonate, polyetherether ketone (PEEK), ultra-high molecular weight polyethylene (UHMWPE) or polyarylamide.

As mentioned, the lower portion 31B is the portion closest to the spinal cage SC or holding position of the cage SC. The lower shaft portion 31B comprises an upper extremity connected to the upper shaft portion 31A and an opposing lower extremity comprising attachment and release means ARA for attaching and releasing the cage SC, or an apparatus ARA configured to attach and release the cage SC.

The attachment and release means or the apparatus ARA can, for example, be actioned to attach and release the cage SC via a rotatable knob KB of the holder 29. Rotation in a first direction permits to open the attachment and release means or the apparatus ARA for reception of the cage SC. Rotation in an opposite second direction permits to close the attachment and release means or the apparatus ARA to complete attachment and results in the cage SC being held or attached to the holder 29. The knob KB is connected to the attachment and release means or the apparatus ARA via an interconnection running centrally inside and through of the holder 29 in an inner chamber (not shown).

The exemplary holder 29 further includes a holder body 27, for example, an elongated holder body 27 attached or fixed to the shaft 31, for example, attached to the extremity of the shaft 31 opposite that for connection to the cage SC, or attached to the extremity of upper shaft portion 31A opposite that connected to the lower shaft portion 31B. The knob KB is, for example, located at an opposing upper extremity to the extremity to which the shaft 31 is attached.

The holder body 27 has a width or diameter W larger than (for example, between 1% and 10% or 20%, or between 3% and 10% or 20%, or between 5% and 10% or 20%) the width or diameter of the shaft 31 or the upper portion 31A of the shaft 31. As shown in FIG. 11, the diameter or width may increase progressively in an outwards or radial direction along the direction of elongation L of the holder body 27 to define at least one contact or impact wall or surface CWS. Alternatively, the contact or impact wall or surface CWS may extend to define a surface that extends outwards or radially (substantially) perpendicular to the shaft 31.

The hammer 1 can be configured to receive the holder body 27 therein and exemplary embodiments are shown in FIGS. 1 to 8 and 9A to 9D. The first cavity 9A and the second cavity 9B have different widths or diameters W. The second cavity 9B has width or diameter W that is larger than the maximum width or diameter MW of the holder body 27 (for example, between 1% and 10% or 20%, or between 3% and 10% or 20%, or between 5% and 10% or 20% larger). The second cavity 9B is for example configured to guide the hammer 1 relative to the holder body 27 to also define a linear movement of the hammer 1 relative to the holder 29.

As mentioned above, the first cavity 9A may have a width or diameter W slightly larger than (for example, between 1% and 10% or 20%, or between 3% and 10% or 20%, or between 5% and 10% or 20%) the width or diameter of the shaft 31 or the upper portion 31A of the shaft 31 to permit the shaft 31 to slide and be guided in the first cavity 9A. This also permits the hammer 1 to be guided linearly and/or guided slidably along the holder 29.

FIGS. 10A to 10E show an exemplary embodiment in which the holder body 27 is not received inside the hammer 1 or inside the cavity 9 of the hammer 1. Guiding is thus assured by the shaft 31 or upper shaft portion 31A inside the cavity 9.

The holder body 27 may, for example, define or have a cylindrical shape or a partially cylindrical shape. The holder body 27 may for example be made of, or comprise or consist of a plastic or a polymer. The holder body 27 is for example made of, or comprises or consists of a polyvinyl chloride (PVC), polyethylene, a polyester, polycarbonate, polyetherether ketone (PEEK), ultra-high molecular weight polyethylene (UHMWPE) or polyarylamide.

The shaft 31 or the lower portion 31B and/or the upper portion 31A of the shaft may, for example, define or have a cylindrical shape or a partially cylindrical shape. The shaft 31 or the lower portion 31B and/or the upper portion 31A of the shaft may for example be made of, or comprise or consist of a metal, for example, stainless steel, or titanium, or tantalum, or platinum, or palladium or aluminum. The upper portion 31A of the shaft may for example be made of, or comprise or consist of a plastic or a polymer. The upper portion 31A is for example made of, or comprises or consists of a polyvinyl chloride (PVC), polyethylene, a polyester, polycarbonate, polyetherether ketone (PEEK), ultra-high molecular weight polyethylene (UHMWPE) or polyarylamide. The upper portion 31A may, for example, comprise a plastic or a polymer covering an inner metallic body or tubing.

The cavity 9 can, for example, extend fully along the entire length of the elongated body 3 and fully through it from the outer extremity TE of the proximal end 5 to the outer extremity BE of the distal end 7.

The elongated body 3 delimits a first opening O1 defining an entrance to the cavity 9 and also delimits a second opening O2 defining another entrance to the cavity 9.

The openings O1, O2 may, for example, have the same diameter or width or different diameters or widths.

The elongated body 3 may delimit or include at least one channel 15 or a plurality of channels 15A, 15B defining the cavity 9 or cavities 9A, 9B. The channel 15 or intercommunicating channels 15A, 15B define the cavity 9 or cavities 9A, 9B configured to receive and guide the shaft 31 of the holder 29 or the body 27 of the holder 29 therein. For example, the portion 31A and/or the portion 31B of the shaft 31 of the spinal cage holder 29 (see for example FIGS. 1 and 11) can be received inside the cavity 9 or the communicating cavities 9A, 9B.

As mentioned, the shaft 31 of the spinal cage holder 29 can comprise at least two portions 31A, 31B of different width or diameter. The lower portion 31B closest to the spinal cage SC or holding position of the cage SC is, for example, of smaller width or diameter relative to the upper portion 31A. This facilitates the attachment of the spinal cage hammer 1 to the spinal cage holder 29. The lower portion 31B can be passed through the slit 11 into the cavity 9 to initially attach the hammer 1 to or place the hammer 1 on the holder 29. The upper portion 31A can then be inserted or slid into the cavity 9 or the first cavity 9A.

Alternatively, the shaft 31 can be of uniform diameter or width. While such a shaft 31 can be used with the hammer 1 of any one of the embodiments of the present disclosure, it is preferably used with the hammer 1 in which the cavity 9 has (substantially) the same width or diameter W, as for example shown in FIG. 10E.

Alternatively, when used with the hammer 1 of FIG. 1 to 8 or 9A to 9B, the holder body 27 interacts with the cavity 9B to guide the hammer displacement and define a linear movement of the hammer 1 relative to the holder 29.

The body 27 of the spinal cage holder 29 in a preferred embodiment has a width or diameter W larger than the width or diameter of the shaft 31. As mentioned, the width or diameter of the body 27 extends radially or laterally outwards from the direction of elongation of the shaft 31. The width of diameter of the body 27 extends, for example, (substantially) in a direction W perpendicular to the direction of elongation L of the body 3, body 27 or shaft 31). This allows an efficient transfer of force from the spinal cage hammer 1 to the spinal cage holder 29.

The channel 15 can, for example, define the cavity 9 having a width or diameter slightly larger than the width or diameter of the shaft 31 or the upper portion 31A of the shaft 31 of the spinal cage holder 29 to permit the shaft 31 to slide and be guided in the channel 15.

The spinal cage hammer 1 includes an interface, wall or surface or an interface wall 17 configured to interface with or contact the body 27 of the spinal cage holder 29. This interface or interface wall 17 contacts the body 27 to allow a transfer of force from the spinal cage hammer 1 to the spinal cage holder 29. The interface, wall or surface 17 defines a force transfer interface, wall or surface. The interface, wall or surface 17 is configured to enter into contact with the spinal cage holder 29 to transfer a force thereto.

The interface wall 17, for example, enters into contact with the at least one contact or impact wall or surface CWS of the holder body 27.

A force is, for example, transferred when the hammer 1 moves relatively to the holder 29 and contacts the holder 29 via the interface wall 17.

The interface wall 17 extends relative to the elongated direction L of extension of the elongated body 3 of the hammer 1 so that the interface wall 17 enters into contact or collision with a portion of the body 27 of the holder 29 permitting a transfer of energy (kinetic energy) from the hammer 1 to the holder 29.

The interface wall 17 extends, for example, non-parallel or (substantially) perpendicular to the elongated direction L of extension of the elongated body 3.

The interface wall or surface 17 may be an internal wall or surface located inside the hammer 1, as shown for example in FIG. 9D. The interface wall or surface 17 is, for example, located at a junction between the first cavity 9A and the second cavity 9B or defines a junction between the first cavity 9A and the second cavity 9B.

The interface wall or surface 17 may alternatively define an external wall or surface of the hammer 1 or be located on an external surface of the hammer 1, as shown for example in FIG. 10C. The interface wall or surface 17 may, for example, define at least a portion of the surface of the outer upper or top extremity TE of the body 3.

The interface wall or surface 17 may be flat or curved. The interface wall or surface 17 and the contact or impact wall or surface CWS of the holder body 27 may, for example, define complementary or matching surfaces/surface profiles. This can permit an increased transfer of force.

The spinal cage hammer 1 may also include a prehension protrusion 23 extending from the elongated body 3. The prehension protrusion 23 can, for example, extend outwards from the elongated body 3 to increase the width or diameter of the elongated body 3. The prehension protrusion 23 can, for example, link two sections of the hammer 1 of different diameters or widths.

The prehension protrusion 23 provides a prehension which can contact the user's hand, for example, the user's thumb and first finger. This allows the Surgeon to maintain a firm grip on the hammer 1 and to apply a large range of force amplitudes to the spinal cage holder 29.

The prehension protrusion 23 may extend progressively outwards. This assures a gentler contact with a user's hand when using the hammer 1.

As for example shown schematically in FIGS. 9A to 9D, the elongated body 3 may, for example, define the first cavity 9A and the second cavity 9B. The first the second cavities 9A, 9B can be directly interconnected. The first and the second cavities 9A, 9B can be directly and continuously interconnected. The first and the second cavities 9A, 9B communicate directly with each other.

As mentioned, the elongated body 3 may delimit the first opening O1 defining an entrance to the first cavity 9A and delimit the second opening O2 defining an entrance to the second cavity 9B. The elongated body 3 may additionally delimit a third opening O3 between the first and second openings O1, O2 and interconnecting the first and second cavities 9A, 9B as shown in the embodiment of FIG. 9C. The third opening O3 is, for example, located at the junction between the first cavity 9A and the second cavity 9B.

The first opening O1 may, for example, have a smaller diameter or width than the second opening O2. The first and third openings O1, O3 may have the same diameter or width.

The elongated body 3 can, for example, delimit or include the first channel 15A defining the first cavity 9A, and delimit the second channel 15B defining the second cavity 9B, as for example shown in FIG. 9D. The first and second channels 15A, 15B are, for example, directly interconnected or directly intercommunicating.

A width or diameter of the first channel 15A can be smaller than the width or diameter of the second channel 15B. The volume of the first channel 15A can be smaller than the volume of the second channel 15B.

The interface wall or surface 17 is, for example, located at a junction between the first channel 15A and the second channel 15B or defines a junction between the first channel 15A and the second channel 15B. The interface wall or surface 17 can, for example, define a portion or a wall of the second channel 15B.

The interface wall 17 can interconnect the first and second channels 15A, 15B. As previously mentioned, the interface wall 17 is configured to interface with and contact the body 27 of the spinal cage holder 29. The interface wall 17 can extend non-parallel or (substantially) perpendicular to the direction of extension L of the elongated body 3.

The first channel 15A defines the cavity 9A which is configured to receive and guide the shaft 31 or the portion 31A of the shaft 31 of a spinal cage holder 29.

The first channel 15A defines the cavity 9A to have a width or diameter slightly larger than a width or diameter of the shaft 31 or the portion 31A of the shaft 31 of the spinal cage holder 29 to permit the shaft 31 to slide and be guided in the first channel 15A.

The second channel 15B defines the cavity 9B configured to receive and guide the body 27 of the spinal cage holder 29. The second channel 15B defines the cavity 9B to have a width or diameter slightly larger than a width or diameter of the body 27 of the spinal cage holder 29 to permit the body 27 to slide and be guided in the second channel 15B.

The prehension protrusion 23 extending from the elongated body 3 allows the Surgeon to maintain a firm grip on the hammer 1 and to apply a large range of force amplitudes to the spinal cage holder 29. The prehension protrusion 23 may be, for example, funnel-shaped.

Advantageously, the spinal cage hammer 1 is, for example, configured to apply a linear force to the spinal cage holder 29, and in particular to apply a linear upwards or downwards force to a spinal cage holder 29.

The spinal cage hammer 1 is attached to the spinal cage holder by passing the shaft 31, for example, the lower portion 31B of the spinal cage holder 29 through the slit 11. This can be done, for example, by inserting the shaft portion 31B into the slit 11 at an angle and then straightening the shaft so that it becomes parallel to channel 15, 15A, 15B with the shaft 31 being inside the channel 15 or channels 15A, 15B.

The spinal cage hammer 1 can then be moved at a desired speed or force upwards along the body 27 so that the body 27 of the spinal cage holder 29 contacts the interface wall 17 of the spinal cage hammer 1 transferring a linear vertical or upward force to the spinal cage holder 29 permitting the spinal cage to be displaced.

The spinal cage hammer 1 with the cage SC attached can be inserted into the spine of a patient. The hammer 1 can be slid and or guided along the holder 29 to apply a force a linear, vertical or upward force, for example in the direction of the user, to the spinal cage holder 29 permitting the spinal cage to be displaced in an upwards direction to or towards a desired position in the spine of the patient. The force applied can be better controlled in amplitude and direction permitting the cage SC to be positioned more easily and more quickly.

The hammer 1 permits a more precise application of a hammering force or impact of a desired amplitude and direction to the spinal cage holder and as a result the insertion and correct placement of a spine cage can be achieved more quickly and without a prolonged effort being required by the Surgeon to achieve correct placement of the spinal cage.

The present disclosure also concerns a spinal cage system including the spinal cage hammer 1 and the spinal cage holder 29 and/or the spine cage SC.

The spinal cage holder 29 may additionally include an attachment 33 configured to be attached to the shaft 31, or the upper portion 31A, or lower portion 31B of the spinal cage holder 29 (see for example FIG. 11). This permits the distal end 7 of the spinal cage hammer 1 to apply a downward force to the spinal cage holder 29. The spinal cage hammer 1 can be moved at a desired speed or force downwards along the body 27 and shaft 31 so that the distal end 7 or the outer extremity BE of the distal end 7 of the spinal cage holder 29 contacts the attachment 33 transferring a linear vertical or downward force to the spinal cage holder 29 permitting the spinal cage SC to be displaced to a desired position.

The attachment 33 can be attached by press-fit or lock fit to the shaft 31 and/or can be held by an adhesive or a weld.

The attachment 33 can be or comprise, for example, a partial annular member or full annular member configured to enclose the shaft 31A, 31B, or to lock to the shaft 31. The shaft 31 may include a groove or annular groove into which the annular member fits.

The attachment 33 may be permanently fixed to the shaft 31, or provisionally attached and thus removable from the shaft 31. When permanently attached, the attachment 33 is attached to the shaft 31 at a location on the shaft that does not impede insertion of the shaft 31 into the hammer 1, that is at a distance sufficiently far from the body 27 of the holder 29.

The attachment 33 may, for example, comprises a pin configured to be received and held in the shaft 31 of the spinal cage holder 29. The shaft 31 includes a corresponding bore or through-hole configured to receive and hold the pin. The pin may include a clip, for example, a hitch pin clip for assuring the maintenance of the pin to the shaft 31.

The attachment 33 has a width or diameter that is larger than the width or diameter of the cavity 9 or first cavity 9A to permit contact and a transfer of force from the hammer 1 to the holder 29.

The present disclosure also concerns sterilized packaging including the hammer 1 and/or the holder 29 and/or the spinal cage SC. The hammer 1 and the holder 29 may be pre-mounted in the sterilized packaging. The hammer 1, the holder 29 and the spinal cage SC may be pre-mounted in the sterilized packaging.

The present disclosure also concerns a method of using the spinal cage hammer 1 including the steps of providing the spinal cage hammer 1, attaching the spinal cage hammer 1 to the holder 29, attaching the spinal cage SC to the holder 29 and slidably displacing the hammer along the holder 29 to apply a force to the holder 29 to position the cage SC in the spine of a patient.

While the invention has been disclosed with reference to certain preferred embodiments, numerous modifications, alterations, and changes to the described embodiments, and equivalents thereof, are possible without departing from the sphere and scope of the invention. The features of any one of the described embodiments may be included in any other of the described embodiments. The methods steps are not necessary carried out in the exact order presented above and can be carried out in a different order. Accordingly, it is intended that the invention not be limited to the described embodiments, and be given the broadest reasonable interpretation in accordance with the language of the appended claims.

The invention claimed is:

1. A spinal cage hammer comprising:
    an elongated body having a proximal end and a distal end, the elongated body including at least one cavity extending from the proximal end to the distal end along an axis of elongation, the at least one cavity being configured to receive a portion of a spinal cage holder configured to hold a spinal cage, the at least one cavity including a first cavity and a second cavity, the first cavity having a smaller diameter or width than the second cavity;
    a contact surface configured to enter into contact with the spinal cage holder to transfer a force to the spinal cage holder, the contact surface being disposed in between the first cavity and the second cavity to enter into contact with a body of the spinal cage holder when the elongated body is moved relative to the spinal cage holder, when holding the spinal cage holder, to transfer the force to the spinal cage holder; and a slit formed substantially in parallel to the axis of elongation, extending fully along the elongated body from an outer extremity of the proximal end to an outer extremity of the distal end and into the at least one cavity and traversing the elongated body entirely.

2. The spinal cage hammer according to claim 1, wherein the elongated body defines
   a first opening defining an entrance to the first cavity, the entrance to the first cavity being configured to receive therein a shaft of the spinal cage holder that extends from a handle of the spinal cage holder, and
   a second opening at the outer extremity of the proximal end of the elongated body, the second opening defining an entrance to the second cavity, the entrance to the second cavity and the second opening being configured to receive and enclose therein the handle of the spinal cage holder, the first opening being smaller in width or diameter than the second opening.

3. The spinal cage hammer according to claim 1, wherein the first cavity is configured to guide the portion of the spinal cage holder.

4. The spinal cage hammer according to claim 1, further comprising:
   a prehension protrusion extending from the elongated body.

5. The spinal cage hammer according to claim 1, wherein the second cavity is configured to at least partially accommodate the body of the spinal cage holder.

6. The spinal cage hammer according to claim 1, wherein the first cavity is dimensioned to receive and guide a shaft of the spinal cage holder.

7. The spinal cage hammer according to claim 6, wherein the slit is configured for passage of the shaft of the spinal cage holder to the first and second cavity in a direction that is perpendicular to the axis of elongation.

8. A spinal cage system comprising:
   a spinal cage holder configured to hold a spinal cage; and
   a spinal cage hammer including
      an elongated body having a proximal end and a distal end, the elongated body including at least one cavity extending from the proximal end to the distal end along an axis of elongation, the cavity configured to receive a portion of the spinal cage holder, the at least one cavity including a first cavity and a second cavity, the first cavity having a smaller diameter or width than the second cavity,
      a contact surface configured to enter into contact with the spinal cage holder to transfer a force to the spinal cage holder, the contact surface being disposed in between the first cavity and the second cavity to enter into contact with a body of the spinal cage holder when the elongated body is moved relative to the spinal cage holder, when holding the spinal cage holder, to transfer the force to the spinal cage holder, and
      a slit formed substantially in parallel to the axis of elongation, extending fully along the elongated body from an outer extremity of the proximal end to an outer extremity of the distal end and into the at least one cavity and traversing the elongated body entirely.

9. The spinal cage system according to claim 8, wherein the second cavity is configured to at least partially accommodate the body of the spinal cage holder.

10. The spinal cage system according to claim 8, wherein the first cavity is configured to guide a shaft of the spinal cage holder.

11. The spinal cage system according to claim 10, wherein the spinal cage holder includes an attachment disposed at the shaft, the attachment configured to engage with the spine cage hammer permitting the distal end of the spinal cage hammer to apply a force to the spinal cage holder.

12. The spinal cage system according to claim 8, wherein the elongated body defines
   a first opening defining an entrance to the first cavity, the entrance to the first cavity being configured to receive therein a shaft of the spinal cage holder that extends from a handle of the spinal cage holder, and
   a second opening located at the outer extremity of the proximal end of the elongated body, the second opening defining an entrance to the second cavity, the entrance to the second cavity and second opening being configured to receive and enclose therein the handle of the spinal cage holder, and
   wherein the first opening is smaller in width or diameter than the second opening.

* * * * *